(12) United States Patent
Heneghan

(10) Patent No.: US 7,150,958 B2
(45) Date of Patent: *Dec. 19, 2006

(54) POLYMERIC MATERIAL, CONTAINING A LATENT ACID

(75) Inventor: Michael Heneghan, Rheinfelden-Eichsel (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 294 days.

This patent is subject to a terminal disclaimer.

(21) Appl. No.: 10/477,362

(22) PCT Filed: Jun. 4, 2002

(86) PCT No.: PCT/EP02/06109

§ 371 (c)(1),
(2), (4) Date: Nov. 12, 2003

(87) PCT Pub. No.: WO02/100914

PCT Pub. Date: Dec. 19, 2002

(65) Prior Publication Data

US 2004/0157947 A1 Aug. 12, 2004

(30) Foreign Application Priority Data

Jun. 12, 2001 (GB) .................. 0114265.2

(51) Int. Cl.
G03F 1/10 (2006.01)
G03F 7/004 (2006.01)
G03F 7/039 (2006.01)
C08L 61/00 (2006.01)

(52) U.S. Cl. .............. 430/281.1; 430/282.1; 430/283.1; 430/284.1; 430/285.1; 430/286.1; 430/287.1; 430/288.1; 524/876; 524/877; 524/878

(58) Field of Classification Search ............. 430/281.1, 430/282.1, 283.1, 284.1, 285.1, 286.1, 287.1, 430/288.1; 524/876, 877, 878
See application file for complete search history.

(56) References Cited

U.S. PATENT DOCUMENTS

| | | | |
|---|---|---|---|
| 4,343,885 A | 8/1982 | Reardon, Jr. ................ 430/177 |
| 5,677,107 A | 10/1997 | Neckers ...................... 430/269 |
| 6,589,641 B1 * | 7/2003 | Stirniman et al. .......... 428/216 |
| 6,787,591 B1 * | 9/2004 | Koch et al. ................. 524/102 |

FOREIGN PATENT DOCUMENTS

| | | |
|---|---|---|
| EP | 0290750 | 11/1988 |
| EP | 0600441 | 6/1994 |
| EP | 0720053 | 7/1996 |

* cited by examiner

*Primary Examiner*—Hoa Van Le
(74) *Attorney, Agent, or Firm*—Shiele A. Loggins

(57) ABSTRACT

Polymeric material, containing a latent acid which can be converted to an acid by irradiation by a laser and optionally further ingredients.

4 Claims, No Drawings

POLYMERIC MATERIAL, CONTAINING A LATENT ACID

The present application relates to polymeric material containing a latent acid, i.e. a compound which is not an acid but which can be converted to an acid by the influence of irradiation.

For specific technical applications, compositions are requested containing compounds which are capable of reacting with acids, however, such a reaction should be suppressed until a predetermined moment. It is common practice in such cases to separate the compounds and the acids by suitable measures, e.g. by encapsulating them into coverings and destroying these coverings when reaction is desired. This method is, however, not practicable in many cases.

The present application describes an elegant solution for that problem by using not acids but latent acids. Thus the compounds capable of reacting with acids can be intimately mixed with the latent acids without reaction. No covering material is required. At the desired moment reaction can easily be achieved by irradiating the mixture in a suitable manner to convert the latent acid into the acid, which then reacts with the compound.

The present application concerns polymeric material, containing a latent acid, which can be converted to an acid by irradiation and optionally further ingredients.

As latent acids compounds are suitable which are not acids per se and contain a proton, which can be split off by irradiation.

Preferred latent acids are compounds of formula

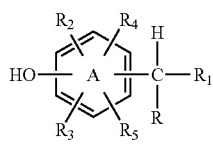

(1)

wherein the ring A can contain one or more hetero atoms and/or can contain an anelated ring, $R_1$ is hydrogen, alkyl, preferably $C_1$–$C_{20}$-alkyl, alkenyl, preferably $C_2$–$C_{20}$-alkenyl, aryl, preferably phenyl or phenyl which is substituted one to three times with $C_1$–$C_4$alkyl, or $C_1$–$C_4$alkoxy, $R_2$, $R_3$, $R_4$ and $R_5$ independently of each other are hydrogen or a functional substituent, and R stands for $C_1$–$C_6$alkyl, -$Z_1$-$Q_1$, or -$Z_2$-$Q_2$, wherein $Z_1$ is a single bond, S, NH or O, and $Q_1$ is a heterocyclic ring system having from 5 to 9 ring atoms selected from C, S, O and N, with at least 2, preferably at least 3, more preferably at least 4 carbon atoms in the ring system, preferably $Q_1$ stands for morpholine, pyridine, which may be substituted one to three times with $C_1$–$C_4$alkyl or hydroxy, mercaptobenzoxazole, mercaptobenzthiazole, and wherein $Z_2$ stands for $C_1$–$C_4$alkylene, which can be substituted by $C_1$–$C_4$alkyl or $Q_3$, wherein $Q_3$ stands for phenyl which can be substituted one to three times with $C_1$–$C_4$alkyl, hydroxy, $C_5$–$C_8$ cycloalkyl and/or a heterocyclic ring system having from 5 to 9 ring atoms selected from C, S, O and N, with at least 2, preferably at least 3, more preferably at least 4 carbon atoms in the ring system, and $Q_2$ stands for phenyl which can be substituted one to three times with $C_1$–$C_4$alkyl, hydroxy, $C_5$–$C_8$cycloalkyl and/or a heterocyclic ring system having from 5 to 9 ring atoms selected from C, S, O and N, with at least 2, preferably at least 3, more preferably at least 4 carbon atoms in the ring system, with the proviso that the hydrogen atom at the C-atom in α-position to R can be split off by irradiation.

Preferably, $Z_2$ stands for —$CH_2$—, —$CH_2$—$CH_2$—, —$CH_2$—$CHMe$-, —$CH_2$—$CHQ_3$-, in which $Q_3$ stands for 4-hydroxy-3-i-propyl-6-methylphenyl, 4-hydroxy-3-tert.-butyl-6-methylphenyl, or 4-hydroxy-3-cyclohexyl-6-methylphenyl and $Q_2$ stands for phenyl or 4-hydroxy-3-i-propyl-6-methylphenyl, 4-hydroxy-3-tert.-butyl-6-methylphenyl, or 4-hydroxy-3-cyclohexyl-6-methylphenyl.

Suitable rings A are e.g. phenyl, naphthyl, pyridyl and quinolinyl, phenyl and pyridyl are especially preferred.

$R_1$ is preferably hydrogen, or methyl.

Functional substituents $R_2$, $R_3$, $R_4$ and $R_5$ are e.g. $C_1$–$C_{20}$-alkyl, preferably $C_1$–$C_8$-alkyl, particularly preferred $C_1$–$C_6$-alkyl, especially preferred $C_1$–$C_4$-alkyl, $C_5$–$C_8$-cycloalkyl, $C_2$–$C_{20}$-alkenyl, preferred $C_2$–$C_6$-alkenyl, $C_1$–$C_6$-alkoxy, hydroxy, halogen, nitro, cyano, —$SO_2R'$, wherein R' is hydrogen, alkyl or a metallic cation such as a alkali metal, e.g. sodium or potassium, or earth alkali metal cation, e.g. calcium, or phenyl, which may be substituted one to three times with hydroxy and/or $Z_{21}$-$R_7$, wherein $Z_{21}$ stands for $C_1$–$C_4$alkylene, which can be substituted by $C_1$–$C_4$alkyl, and $R_7$ stands for hydrogen, $C_1$–$C_4$alkyl or phenyl, which may be substituted one to three times with hydroxy, $C_1$–$C_4$alkyl and/or $Z_{22}$-$R_8$, wherein $Z_{22}$ stands for for $C_1$–$C_4$alkylene, which can be substituted by $C_1$–$C_4$alkyl, and $R_8$ stands for a heterocyclic ring system having from 5 to 9 ring atoms selected from C, S, O and N, with at least 2, preferably at least 3, more preferably at least 4 carbon atoms in the ring system, preferably $R_8$ stands for morpholine. In a preferred embodiment of this invention $R_2$, $R_3$, $R_4$ and $R_5$ are preferably independently of each other hydrogen, $C_1$–$C_{20}$-alkyl or $C_2$–$C_{20}$-alkenyl or substituted phenyl wherein hydroxy and $Z_{21}$-$R_7$ being the substituents. Especially preferred compounds of formula (1) are those wherein $R_2$ and $R_3$ are independently of each other $C_1$–$C_8$-alkyl and $R_4$ and $R_5$ are each hydrogen.

Halogen means fluoro, chloro, bromo, or iodo, preferably chloro.

Heterocyclic residue or heterocyclic ring system having at least 2, preferably at least 3, more preferably at least 4 carbon atoms means e.g. an optionally substituted monocyclic or bicycliclic heterocyclic residue such as pyrrolidino, piperidino, morpholino, benzthiazole, 1,2,4-triazole, imidazole, pyrazole, tetrazole, thiazolin-2-thione, imidazolin-2-thione, N-methylimidazolon-2-thione and 5-(3-phenyl-1,3, 4-thia-diazol-2(3H)-thione), 2-pyridine, 4-pyridine, 3-pyridazine, 2-pyrimidine, 2-thiazole, 2-thioazoline, 3-(1, 2,4-triazole) and 5-(2-mercapto-1,3,4-thiadiazole), naphthyridine, purine and pteridine residues, benzimiazole, benzotriazole, benzoxazolin-2-thione, 2-benzoxazole, mercaptobenzoxazol, mercaptobenzthiazol and quinolinyl.

It is furthermore preferred that at least one of $R_2$ and $R_3$ is in o-position to the OH-group.

The organic residue R can be of any kind with the proviso that the hydrogen atom at the C-atom in α-position to R can be split off by irradiation. Preferably R is a heterocyclic residue which is bond via a nitrogen, oxygen or sulfur atom or is a $C_1$–$C_6$-alkyl which is unsubstituted or substituted, e.g. by hydroxy, $C_1$–$C_6$-alkoxy or unsubstituted or substituted aryl, especially phenyl. Suitable substituents for aryl are preferably the above-mentioned substituents $R_2$ through $R_5$.

Most preferably R is a radical of mercaptobenzoxazol or mercaptobenzthiazol or $C_1$–$C_4$-alkyl which is unsubstituted or substituted by unsubstituted phenyl or phenyl carrying 1 to 4 substituents selected from the group consisting of $C_1$–$C_6$-alkyl, $C_1$–$C_4$-alkoxy and hydroxy.

In preferred compounds of formula (1) the residue —CHRR$_1$ is situated in o- or p-, especially in p-position to the OH-group.

$C_1$–$C_{20}$-alkyl means e.g. methyl, ethyl, n-, i-propyl, n-, sec.-, iso-, tert.-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, preferably $C_1$–$C_8$-alkyl such as methyl, ethyl, n-, i-propyl, n-, sec.-, iso-, tert.-butyl, n-pentyl, n-hexyl, n-heptyl, n-octyl, particularly preferred $C_1$–$C_6$-alkyl such as methyl, ethyl, n-, i-propyl, n-, sec.-, iso-, tert.-butyl, n-pentyl, n-hexyl, especially preferred $C_1$–$C_4$-alkyl such as methyl, ethyl, n-, i-propyl, n-, sec.-, iso-, tert.-butyl.

$C_5$–$C_8$-cycloalkyl stands for cyclopentyl, cyclohexyl, cycloheptyl, or cyclooctyl, preferably cyclohexyl.

$C_2$–$C_{20}$-alkenyl stands for e.g. ethenyl, n-, i-propenyl, n-, sec.-, iso-, tert.-butenyl, n-pentenyl, n-hexenyl, n-heptenyl, n-octenyl, n-nonenyl, n-decenyl, n-undecenyl, n-dodecenyl, n-tridecenyl, n-tetradecenyl, n-pentadecenyl, n-hexadecenyl, n-heptadecenyl, n-octadecenyl, n-nonadecenyl, n-eicosenyl, preferably $C_2$–$C_6$-alkyl such as ethenyl, n-, i-propenyl, n-, sec.-, iso-, tert.-butenyl, n-pentenyl, n-hexenyl.

$C_1$–$C_6$-alkoxy stands for e.g. methoxy, ethoxy, n-, i-propoxy, n-, sec.-, iso-, tert.-butoxy, n-pentoxy, n-hexoxy.

Preferred polymeric material according to the present invention contains a latent acid of formula (1) wherein
the ring A is phenyl or pyridyl,
R$_1$ is hydrogen,
R$_2$ and R$_3$ are independently of each other $C_1$–$C_4$-alkyl,
R$_4$ and R$_5$ are each hydrogen and
R is a heterocyclic residue, which is bond to the CHR$_1$-group via a nitrogen, oxygen or sulfur atom or is a $C_1$–$C_6$-alkyl, which is unsubstituted or substituted.

Especially preferred compounds of formula (1) are the following compounds:

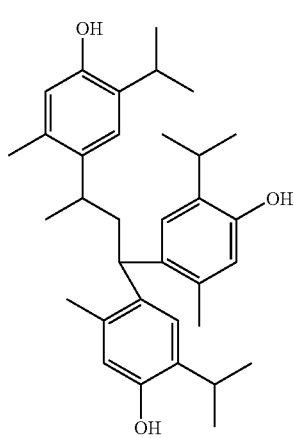
(2)

-continued

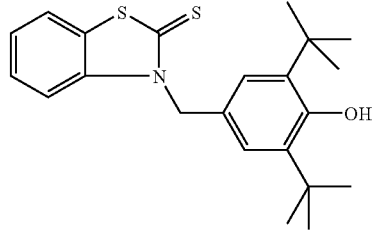
(3)

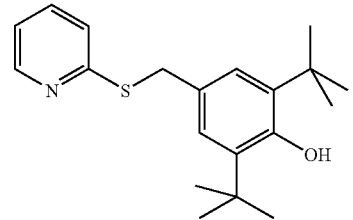
(4)

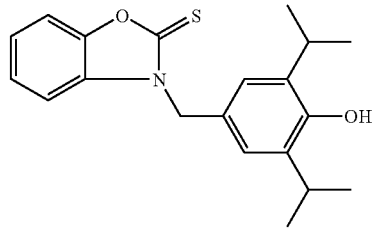
(5)

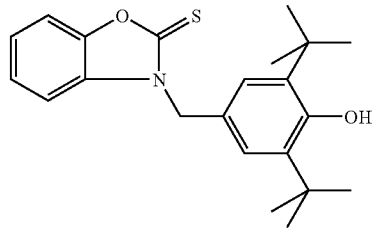
(6)

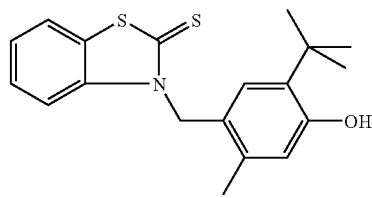
(7)

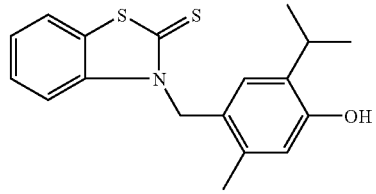
(8)

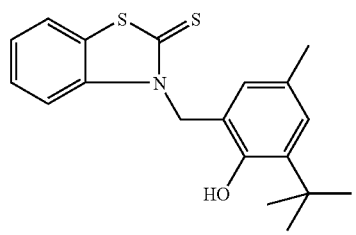
(9)

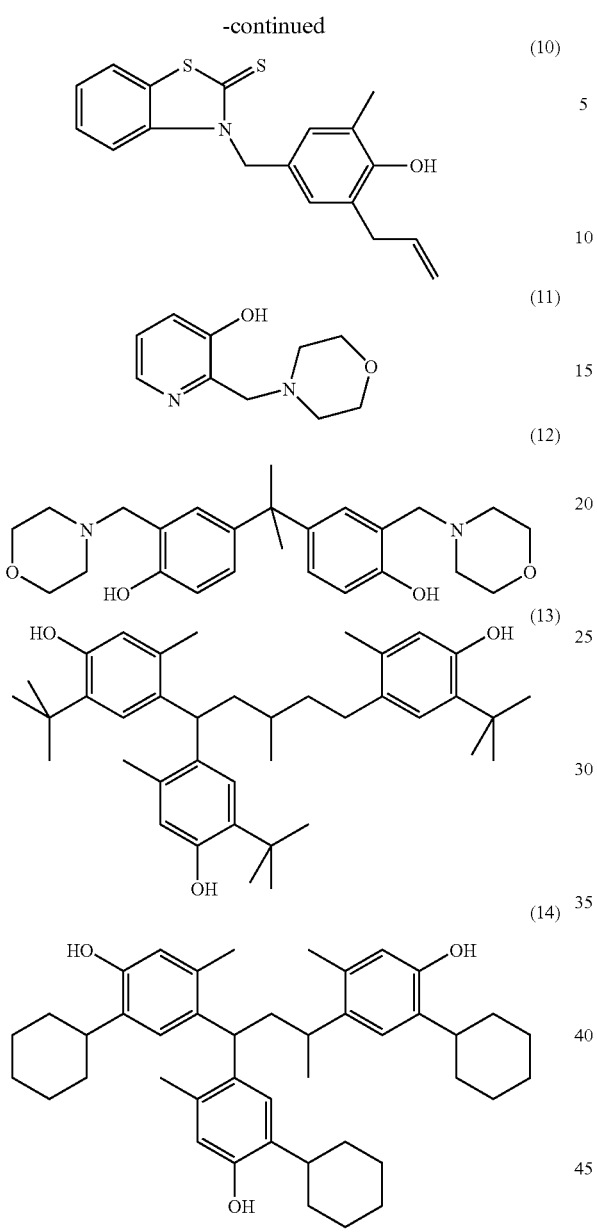

The compounds of formula (1) are known or can be made in a manner known per se, e.g. compound (2) according to GB 2,120,243 and compounds (5) and (6) as described in EP-A-330 613.

The compounds of the above formulae (7) and (8) are new. These compounds also form part of the subject matter of the present invention. They can be obtained in a conventional manner by reaction of mercaptobenzothiazole with a 2,5-dialkylphenol and paraformaldehyde.

Polymeric material useable for the present invention is preferably synthetic organic polymeric material, especially material commonly used for electronic applications.

In particular the following polymers are preferred:
1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
 a) radical polymerisation (normally under high pressure and at elevated temperature).
 b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copollymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EM), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

Homopolymers and copolymers from 1.)–4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).
6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes, which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.
20. Polyketones.
21. Polysulfones, polyether sulfones and polyether ketones.

22. Crosslinked polymers derived from aldehydes on the one hand and phenols, ureas and melamines on the other hand, such as phenovformaldehyde resins, urea/formaldehyde resins and melamine/formaldehyde resins.
23. Drying and non-drying alkyd resins.
24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Crosslinkable acrylic resins derived from substituted acrylates, for example epoxy acrylates, urethane acrylates or polyester acrylates.
26. Alkyd resins, polyester resins and acrylate resins crosslinked with melamine resins, urea resins, isocyanates, isocyanurates, polyisocyanates or epoxy resins.
27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without α-celerators.
28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Especially preferred is organic polymeric material made of SAN (copolymer made of styrene and acrylonitrile), PP (polypropylene), PE (polyethylene), PVC (polyvinylchloride), PET (polyethyleneterephthalate), PET-G (glycole-modified PET), PMMA (polymethylmethacrylate) and related polyacrylics, PS (polystyrene), ASA (copolymer made of acrylonitrile, styrene, acrylate), PA (polyamide), ABS (copolymer made of acrylonitrile, styrene, butadiene), LLDPE (linear LDPE), LDPE (low density polyethylene), HDPE (high density polyethylene) and polycarbonate, most preferably polycarbonate. The polymeric material can also be a mixture of two or more different polymers.

The polymeric material usually contains preferably 0,001 to 10% by weight, most preferably 0,01 to 5% by weight of the latent acid (1). The polymeric material may also contain mixtures of two or more of the latent acids.

The polymeric material and the latent acid usually form a homogenous mixture. For specific applications, however, compositions can be made in which the latent acid is enriched in a specific part of the polymeric material, e.g. in the surface areas.

The methods for incorporating the latent acid into the polymeric material are in principle known. It is e.g. possible, to dissolve the components in a solvent and then to remove the solvent by evaporation. Another possibility is to melt polymeric material together with the latent acid to get a homogeneous mixture or to thoroughly knead a mixture of polymeric material and latent acid, or to polymerize the corresponding monomers in the presence of the latent acid.

In another embodiment of this invention, the latent acid (1) is grafted on the polymer material by means known in the art. E.g. the latent acid (1) is converted into a monomer, i.e. by incorporating a functional polymerizable group, or a monomer is used which is functionalized with a latent acid group. This allows a graft polymerization on the existing polymeric material or a copolymerization during the manufacturing the polymeric material.

The polymeric material usually may contain further ingredients, e.g. stabilizers, antioxidants, softeners etc. as are commonly used for polymeric material.

To convert the latent acid into the corresponding acid, the polymeric material is irradiated. Irradiation in this application especially means irradiation with UV-light and especially with UV-lasers.

As a rule, the lasers used are commercially available. The wavelength of the UV-light preferably is chosen in the range of 285 to 400 nm, particularly preferred in the range of 285 to 370 nm. The duration of irradiation depends on the components and on the type of UV-source and be easily be determined by simple experiments.

The inventive polymeric material containing a latent acid can be used in a system for laser decoration if the polymeric material additionally contains a colourless colour former which gives a visible colour after reaction with an acid.

The following non-limitative examples illustrate the invention in more detail. Parts and percentages are by weight, unless otherwise stated.

EXAMPLES

Example 1

To a reaction flask are charged 16.7 g of mercaptobenzothiazole, 16.4 g 2-t-butyl-5-methylphenol, 3.0 g paraformaldehyde and 1 ml dibutylamine. The mixture is heated to 120° C. and held at this temperature for 6 hours. After cooling to room temperature 75 ml ethanol are added. Then the mixture is heated to reflux for 2 hours and then cooled to 20° C. and filtered. By trituration of the product with hot methanol a product with melting point 177.9–183.9° C. is obtained. The product is of the following formula:

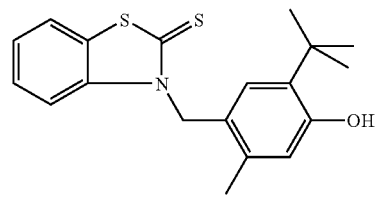

Yield 22.5 g (65.6% theory).

Example 2

Repeating example 1, but replacing 2-t-butyl-5-methylphenol by 15.0 g thymol gives a compound of formula

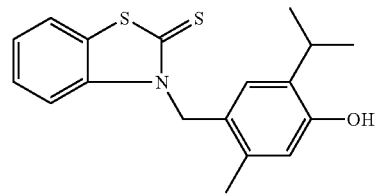

Melting point 119.3–123.0. Yield 9.6 g (29.2% theory).

Example 3

100 parts of polycarbonate, and 1 part of the latent acid according to example 1 and 1 part of the colour former of the formula

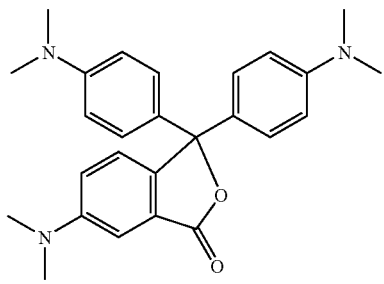

are dissolved in tetrahydrofurane. The solvent is allowed to evaporate overnight. A colourless homogeneous polymeric material is obtained. Irradiation with a UV-laser at 355 nm produces blue marks at the irradiated areas.

Examples 4 to 8

In a similar manner to example 3 the following latent acids are incorporated in polycarbonate:

| Example | Latent Acid | Parts latent acid | Parts Colour Former |
|---|---|---|---|
| 4 | Compound (2) | 1 | 1 |
| 5 | Compound (8) | 1 | 1 |
| 6 | Compound (11) | 1 | 1 |
| 7 | Compound (12) | 1 | 1 |
| 8 | Compound (13) | 1 | 1 |

In each case irradiation with a laser at 355 nm produced a clear blue mark.

The invention claimed is:

1. Process for converting a polymeric material, containing a latent acid, which can be converted to an acid by irradiation by laser, and optionally further ingredients, into polymeric material containing an acid, characterized in that the polymeric material containing a latent acid is irradiated with UV-light and characterized in that the latent acid in the polymeric material is a compound of the formula

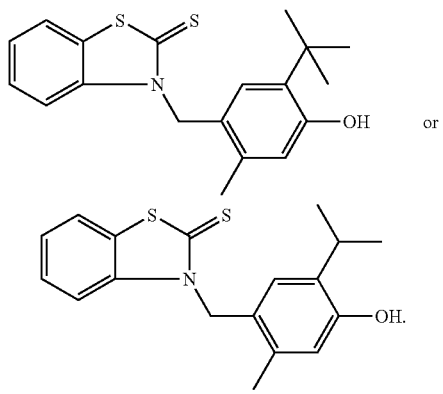

or

2. Polymeric material obtained by a process according to claim 1.

3. Compound of formula

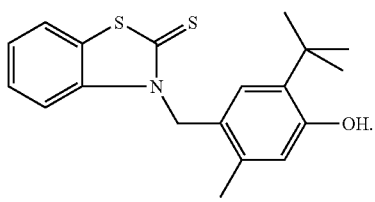

4. Compound of formula

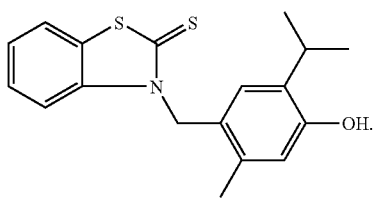

* * * * *